United States Patent [19]

Petragallo

[11] Patent Number: 5,758,658

[45] Date of Patent: Jun. 2, 1998

[54] COMPACT HUMAN RANGE OF MOTION MEASUREMENT SYSTEM

[76] Inventor: Michael R. Petragallo, P.O. Box 2566, Kirkland, Wash. 98083

[21] Appl. No.: 476,873

[22] Filed: Jun. 7, 1995

Related U.S. Application Data

[60] Division of Ser. No. 203,995, Feb. 28, 1994, Pat. No. 5,588,444, which is a continuation-in-part of Ser. No. 978,587, Nov. 19, 1992, abandoned.

[51] Int. Cl.[6] .................................................. A61B 5/00
[52] U.S. Cl. ................................ 128/782; 128/774
[58] Field of Search ............................ 128/782, 774; 33/355 R, 365, 511, 512, 379

[56] References Cited

U.S. PATENT DOCUMENTS

| | | | |
|---|---|---|---|
| 2,565,381 | 8/1951 | Leighton | 33/221 |
| 3,429,052 | 2/1969 | Hembd et al. | 33/220 |
| 4,485,825 | 12/1984 | Domján | 128/774 |
| 4,528,990 | 7/1985 | Knowles | 128/782 |
| 4,665,928 | 5/1987 | Linial et al. | 128/782 |
| 4,777,965 | 10/1988 | Allison et al. | 128/781 |
| 4,928,709 | 5/1990 | Allison et al. | 128/782 |
| 5,188,121 | 2/1993 | Hanson | 128/781 |

FOREIGN PATENT DOCUMENTS

| | | | |
|---|---|---|---|
| 3525756 | 12/1986 | Germany | 128/781 |

OTHER PUBLICATIONS

"Procedure for Measuring Back Motion With the BROM"—product literature from Performance Attainment Associates of Roseville, Minnesota, author unknown (1990).
CROM advertisement at p. 4 of Activator Methods, Inc. Update vol. 7, No. 2 Mar./Apr. 1992 issue, Author unknown.

*Primary Examiner*—Sam Rimell
*Attorney, Agent, or Firm*—Patrick M. Dwyer

[57] ABSTRACT

A modular ROM measurement system is disclosed. A transometer has a horizontal support surface on which are mounted a magnetic north seeking means and leveling means for measurement in a transverse plane. Releasably attached to the horizontal support surface is at least one additional modular component selected from the group of components consisting of an inclinometer for determining degree of inclination of the horizontal support surface from the horizontal, a headband, a stabilizer plate, one or more elastic bans, one of more vertical mode plates selected from the group of plates consisting of a thorax plate and an extremity plate, and one or more soft level adjusting means. Each of the modular components from the above group of components may be releasably attached and temporarily engaged with one another and the horizontal support surface of the transometer, so that a plurality of separate instrument configurations may each be temporarily assembled for performing a specific ROM measurement function, and then be disassembled for compact storage or for reassembly into the same or different configurations.

4 Claims, 9 Drawing Sheets

COMPACT HUMAN RANGE OF MOTION MEASUREMENT SYSTEM

This application is a divisional application of application Ser. No. 08/203,995 filed Feb. 28, 1994 entitled HUMAN RANGE OF MOTION MEASUREMENT SYSTEM, now U.S. Pat. No. 5,588,444 which is a continuation in part of application Ser. No. 07/978,587, filed Nov. 19, 1992, now abandoned.

TECHNICAL FIELD

The invention relates to method and apparatus for measuring human range of motion.

BACKGROUND OF THE INVENTION

Changes in anatomical range of motion between various joints in the body are used to assess and evaluate recovery or treatment of physical injuries and the like. Accurate, reproducible measurement of range of motion in the various joints is very important.

In the measurement of transverse range of motion there are many devices that approach specific monitoring of a patient's capabilities. The goniometer is one that uses two blades that are joined compass fashion at one end with a rivet and spread open to compare the difference from a normal centered position with one blade to the endpoint motion measured by the other blade. This is medium in accuracy.

The CROM and BROM devices are two accurate mechanisms that monitor a singe area per each device. The CROM measures the cervical region, the BROM measures the torso region. Both devices are sizable, a full headgear for the CROM and a magnetic belt and acrylic compass plate for the BROM.

The problems associated with the body measurement in the transverse rotational mode are (a) that no one device can cover the whole body accurately, (b) that the devices now available to externs and new practitioners are expensive with their financial position, and (c) that the size and or setup time is not at maximum efficiency for the patient or clinic convenience. These problems are made more critical by the need to conduct most ROM measurements in a weight bearing mode.

Devices are available that measure certain areas of the body such as the cervicals only or thoracics only and that yield accurate readings, but any device that up to now has approached the full range of body readings for ROM have been low in reliable, repeatable findings.

Measuring the motion of a portion of a human body relative to another has been done utilizing a variety of instruments including compass-type angle indicators or goniometers, pendulum type inclinometers, magnetic compass needles and the like. Also caliper type devices like the spondylometer have been used to measure the motion of the thoracic and lumbar spine relative to the sacrum. Other instrumentalities have been proposed as well to measure spinal and cervical range of motion (hereinafter referred to for convenience as "ROM") for flexion and extension relative to the sacrum or other anatomical reference point, as well as lateral bending and rotation of the vertebrae, and to measure ROM of various extremities. These devices all generate a variety of errors within the measurement methods associated therewith, including rocking induced errors for inclinometers positioned on the sacrum, dorsal vertebral protuberances, or other measurement points on the anatomy.

In single inclinometer measurement systems, the inclinometer must be repositioned repeatedly to measure a ROM for both flexion and extension, introducing errors commonly associated with shifting reference points. Reproducibility suffers or disappears when such devices can not relocate the previously attained measurement point during either subsequent testing or inter-examiner evaluationbeacuse of failure to establish measurement landmarks. Measurement of rotational motion in the torso and neck is similarly plagued with errors.

But the development of devices which are removably and stably mountable to the spine or other human body parts, and that do not require any repositioning of the device during the measurement process, while yielding accurate, verifiable, and reproducible data has not yet been accomplished. Standardization of measurement protocol, particularly standardization to a single measurement system adaptable to every portion of the human anatomy, is a prerequisite to obtaining objective and comparative measurements for a single patient and for adding to the body of therapeutic literature. This has not happened yet either.

What is needed is a system for measuring ROM that employs removable devices that can be temporarily but stably mounted to the anatomical region so as to minimize or eliminate rocking of the device during measurement, while at the same time facilitating highly reproducible measurements. It should be simple in design and operation, not costly, compact, lightweight, and multifunctional.

Previous attempts to address the problems summarized above in general require adjustment of the patient to the measuring instrument, rather than adjustment of the instrument to the patient.

SUMMARY OF THE INVENTION

Accordingly, it is an object of the invention to provide a system for measuring ROM that employs removable devices that can be temporarily but stably mounted to an anatomical region so as to minimize or eliminate rocking of the device during measurement, while at the same time facilitating highly reproducible measurements.

It is a further object of the invention to provide both simple design and operation that is not costly, but is compact, lightweight, and multifunctional.

It is another object of the invention to provide means for hands free operation for patient stabilization during tests.

It is yet another object of the invention to meet any or all of the needs summarized above.

These and other objects of the invention that will become evident from the disclosure below are met by the invention disclosed herein.

The invention addresses ROM measurement of the cervical, thoracic and lumbar vertebrae, and of the extremities, for any and all possible transverse and vertical measurements. Application of the invention to measurement of the extremities is especially beneficial in that there is no device at present that will measure accurately supination, pronation, internal and external rotation, radial/ulnar deviation, or supine ab- and adduction of the upper and lower extremities, to name but a few of the possibilities. Devices incorporating the invention are affordable to a market that needs specific yet economical means to measure patient parameters. The size of such devices is generally small, and some embodiments can fit in a pocket, and they are designed for quick set up and fast usage by those skilled in the art for patient and clinical convenience.

The invention is designed in the component concept so that the practitioner (also sometimes referred to here as the examiner) can assemble a monitoring device from the component parts to measure any possible ROM.

The invention provides a method of ROM measurement for eliminating the error of patient compensation with the following steps:

a) selecting a measurement site at which ROM is to be measured on a patient;

b) applying a first ROM measurement device having anatomical zeroing means to said measurement site and zeroing the device;

c) applying a second ROM measurement device having anatomical zeroing means to a reference site and zeroing the device;

d) causing patient to move through a ROM to a ROM endpoint, and recording the angular readings of both measurement devices;

e) subtracting the reading from the second device from the reading of the first device to arrive at a true ROM reading for the patient at the measurement site.

The invention also provides a modular ROM measurement system. It has a first transometer having a horizontal support surface on which are mounted a magnetic north seeking means, such as a compass, and a leveling means, such as a bubble level, all for measurement in a transverse plane; and one or more of the following components: an inclinometer for determining a degree of inclination of the horizontal support surface from the horizontal; a headband; a stabilizer plate; one or more elastic bands; one or more vertical mode plates such as a thorax plate or an extremity plate; one or more soft level adjusting means, such as bit of soft sponge; a second transometer; each of the above components also having means for releasably interengaging one another and the first transometer. In the invention, a plurality of instruments may each be temporarily assembled from the above first transometer and components, or from a plurality of components, into a configuration for performing a specific ROM measurement function, and then be disassembled for compact storage or for reassembly into the same or different instrument configurations. Preferred embodiments will have a slip ring zeroing dial on the compass.

The invention also provides a transometer having a horizontal support surface on which are mounted a magnetic north seeking means and a leveling means for measurement in a transverse plane. This embodiment is further provided with means to facilitate use of the transometer in both horizontal and vertical measuring modalities. Preferably this further means is a slot/lip structure formed from a lip bent under said horizontal support surface; and a vertical mode plate, which is a plate with a right angle projection. The projection has a slot/lip structure formed from a lip bent over the projection so the respective slot/lip structures may be removably interengaged with one another. Thus the transometer may be used in a vertical modality when it is interengaged with the vertical mode plate, or in a horizontal modality when disengaged from a vertical mode plate. Optionally, a pair of support feet are disposed on an underside of the support surface at opposite ends of the transometer.

The transometer can make use of soft level adjusting means for adjusting said transometer to a level position when it is in use in horizontal mode on a curved surface, such as on top of a human head. In preferred embodiments, a bit of rubber sponge is tucked under one or both ends of the transometer in conjunction with its headband or strap arrangement to level the transometer in conjunction with the use of the bubble level.

The invention also provides an inclinometer for use in a ROM measurement system. The inclinometer has a pair of support feet disposed on an underside of it at its opposite ends so the inclinometer can be held to or applied to a region of an irregular surface for measuring an inclination of that region by "cutting the arc". In a preferred embodiment, the spacing and positioning of the feet is adjustable.

The inclinometer is preferable used in physical combination with a transometer apparatus in some ROM measurement modalities. But an inclinometer can frequently be used beneficially in combination with a second inclinometer, particularly when it is desired to avoid the effects of natural "patient compensation".

The invention also provides a stabilizer bar for use with a transometer in vertical modality for horizontally stabilizing the transometer, and for scoliosis monitoring.

BEST MODE OF CARRYING OUT THE INVENTION

Turning now to the drawings, the invention will be described in detail in a preferred embodiment by reference to the numerals of the drawing figures wherein like numbers indicate like parts.

Figure 1:
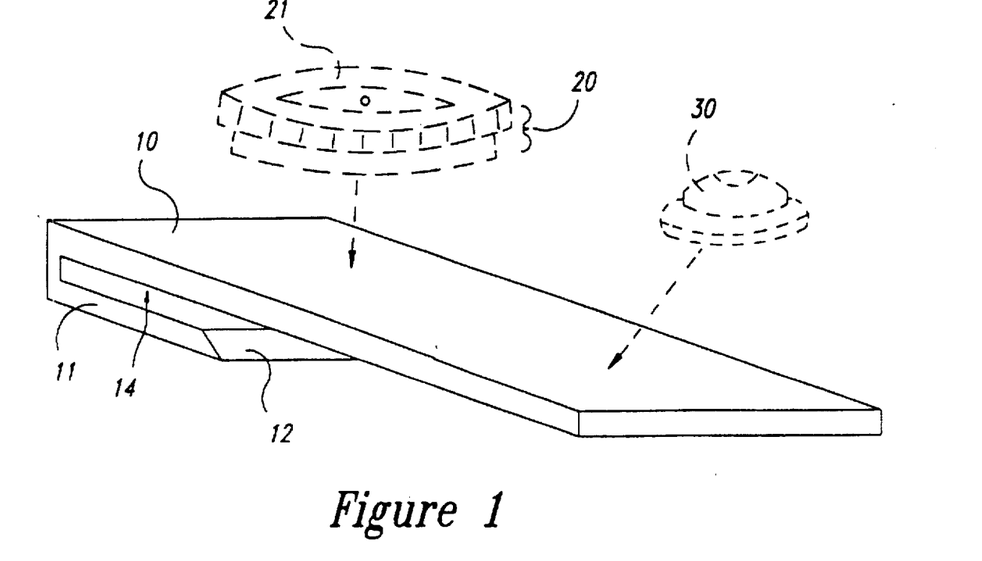
FIG. 1 is a perspective view of an embodiment of the transometer aspect of the invention.

In FIG. 1 a first support plate or horizontal support surface 10 of transometer 5 supports a magnetic north seeking means (preferably a common compass mechanism) 20 which has a rotatable calibrated slip ring dial or zeroing means 21 and a leveling means in the preferred form of a bubble level 30. "Horizontal" or "transverse" as used herein means generally perpendicular to the pull of the earth's gravity, or generally parallel to the earth's curvature or horizon. A bubble level is used in the transometer aspect of the invention to insure the absence of needle drag and a "free needle" reading by showing the examiner the meter's exact incline in all transverse directions.

A compass mechanism is a preferred magnetic north seeking means, with the above calibrations, and is preferably affixed to a clear acrylic resin plate.

Support plate 10 bends at its rear with two 90 degree angles that produce a second level or lip 11 that runs underneath and parallel to the surface 10 above but is shorter in length to define a slot 14 for interconnecting with vertical mode plate 42, whether as back plate, or breast plate (also referred to herein as thorax plate). The front edge of this second level or lip 11 has a bevel 12 to allow easy insertion into slot 14 of lip 40 of vertical mode plate 42 (FIG. 2) (illustrated in the form or extremity plate), when transometer 5 is being used for thoracic, lumbar, or extremity monitoring.

A piece of hook and loop (also know as hook and pile and typified by VELCRO brand closure tape) material 13 is attached to the bottom of plate 10 (FIG. 5) for connection of the headband 70 by way of a piece of the hook and loop material 72 (FIG. 5, 6) when transometer is being used for cervical rotational monitoring.

Figure 2:
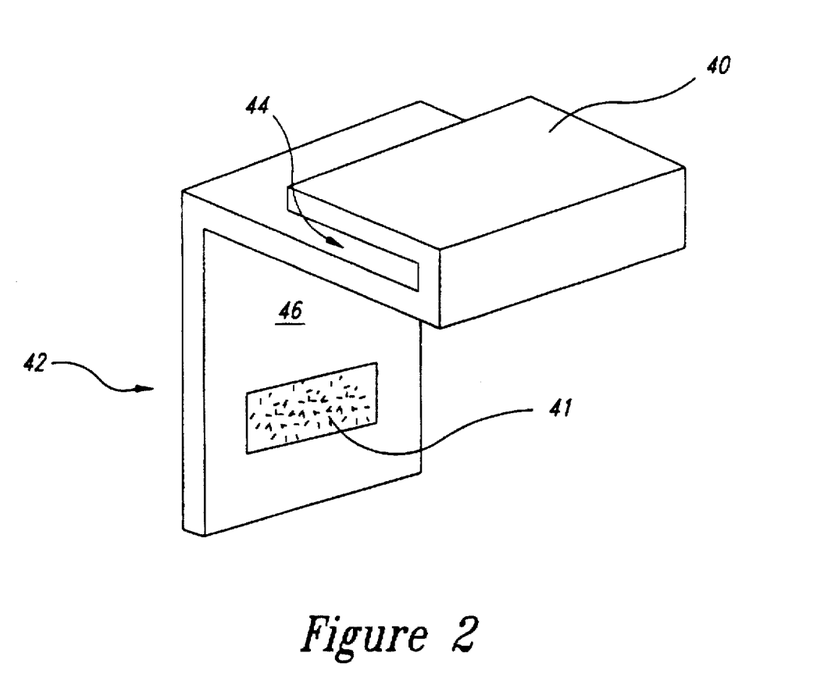
FIG. 2 is a perspective view of an embodiment of the vertical mode plate aspect of the invention.

In FIG. 2 a second support plate in the form of an extremity plate 42 embodiment of the more generally characterized vertical mode plate is illustrated for preferred use with transometer 5 as described above. This figure also schematically illustrates the thorax and back plate aspects of the invention. "Vertical mode", as opposed to "horizontal mode", or measurement means using the transometer against a vertical (ie generally aligned with the pull of the earth's gravity) surface or body contour (such as the back), as opposed to using it on a horizontal or transverse surface or contour (such as the top of the head).

In the figure, the top level of extremity plate 42 is lip 40 which removably slides into slot 14 of transometer 5, giving transometer 5 a 90 degree angle of stabilization to the vertical back surface 45 of plate 42 that is placed in contact with the patient.

A hook and loop attachment strip 41 is placed on front surface 46 of plate 42, and another strip 43 is placed on back surface 45. Back attachment site 43 is for connecting thoraco-lumbar stabilizer bar 50 by way of hook and loop site 51 (FIG. 3), and front attachment site 41 is for connection to the elastic cervical chin strap/extremity strap embodiment of elastic band 60 via hook and loop attachment site 61 (FIG. 40).

Figure 3:
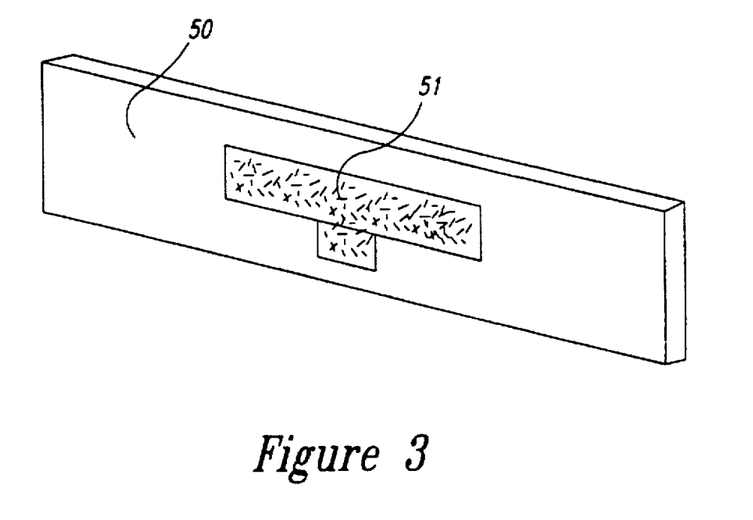
FIG. 3 is a perspective view of an embodiment of the stabilizer bar aspect of the invention.

In FIG. 3 thoraco-lumbar stabilizer bar 50 has hook and loop strip 51 for attachment to extremity plate 42's strip 43, for use when monitoring thoracic and lumbar transverse rotation to maintain an easy to handle perpendicular plane with the torso segment being measured.

Figure 4:
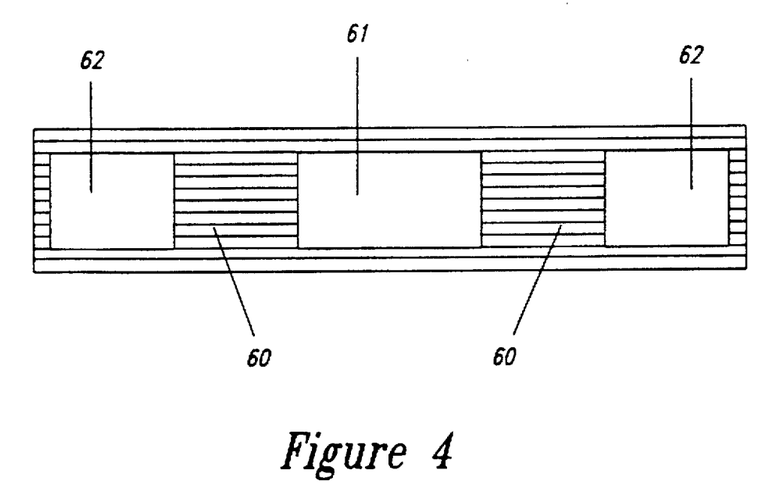
FIG. 4 is a front elevation of an embodiment of the elastic band aspect of the invention.
Figure 5:
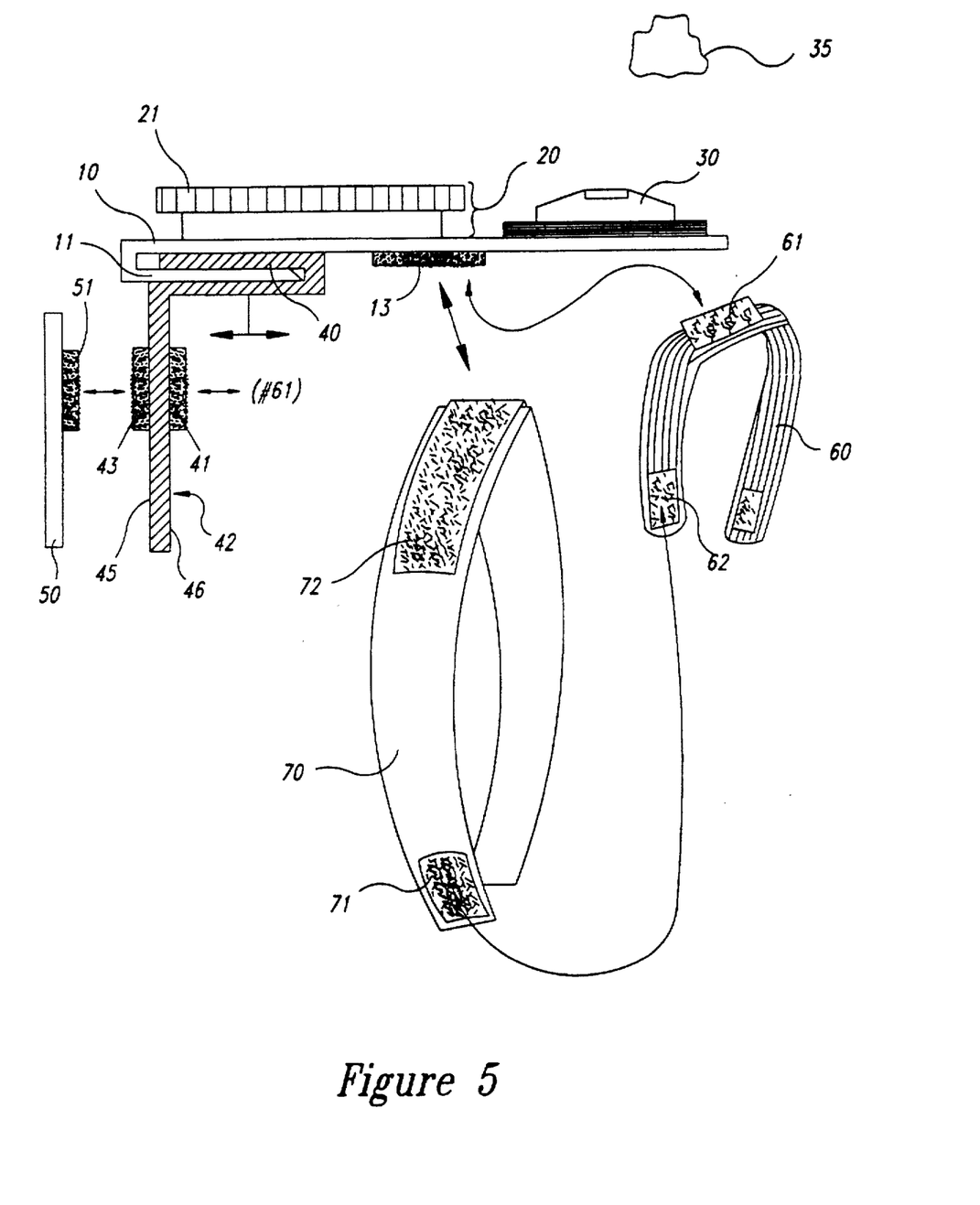
FIG. 5 is a side elevation of an embodiment of invention, combined with a perspective view of an embodiment of the headband aspect and the elastic band aspect of the invention.
Figure 6:
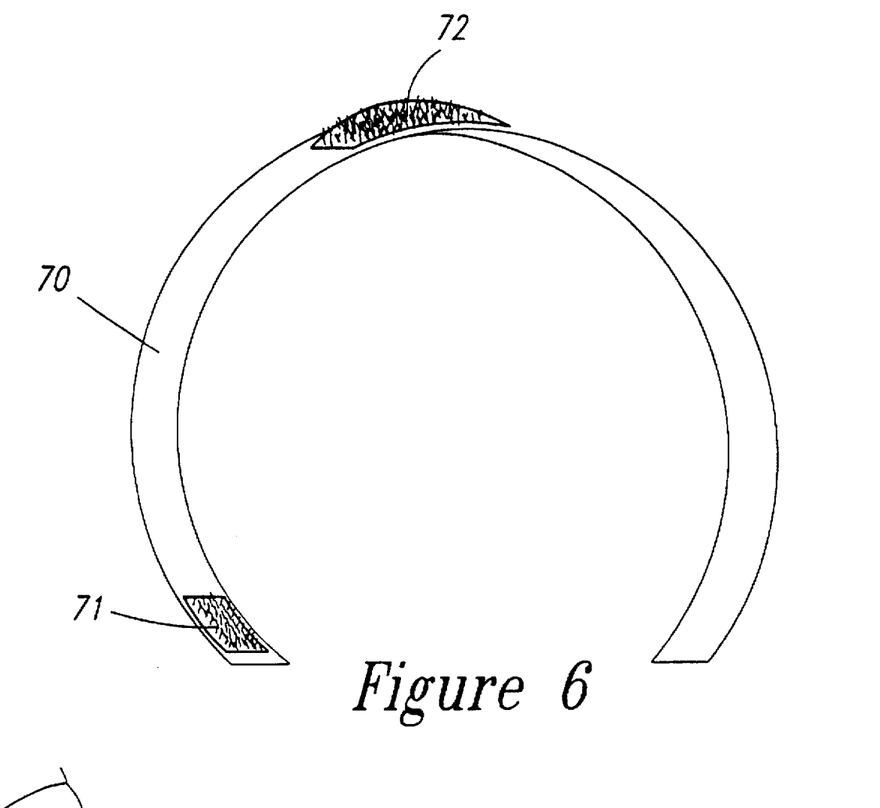
FIG. 6 is a perspective view of an embodiment of the headband aspect of the invention.

In FIG. 4 elastic belt or band 60 is schematic of various embodiments of elastic bands and straps used with the invention, such as the cervical chin strap having hook and loop material 62 on both ends for attachment of the strap 60 to the ends of headband 70 at its tip attachment sites 72 (FIG. 5, 6). It also has attachment site 61 for attachment as an extremity strap to the front of extremity plate 42 via attachment site 41. Preferred material for band 60 is commonly available elastic nylon band.The elastic belts with their hook and loop attachment sites wrap around wrists, chest, forearms, biceps, ankles, and feet.

FIG. 5 illustrates various component combinations in configuring transometer 5, in particular the most commonly used attachment sites when preparing to monitor rotation anywhere on the body, as follows:

Cervical Rotation—1st support plate 10 via strip 13 to strip 72 of headband 70, using elastic strap 60 for a snug fit if necessary via strip 71 to strip 62.

Thoracic Rotation—2nd support plate lip 40 is slid between plate 10 and lip 11; thoraco-lumbar stabilizer bar 50 is attached to the rear hook and loop strip 43 of 2nd support plate 42 by its own hook and loop strip 51.

Lumbar Rotation—same as for thoracic rotation.

Extremity Rotation—(Vertical)—2nd support plate (extremity plate) 42 is attached same as above to 1st support plate (horizontal support surface) 10; center hook and loop strip 61 of elastic strap 60 is attached to front hook and loop strip 41 of 2nd support plate 42 (expected to be the most used combination); (Horizontal)—Strip 61 attached to strip 13, and then two ends of belt 60 attach together at one site 62 and another site of the opposite hook and loop material type (not shown) at the other end of the belt. The band 60 is thus attached together, around the hand for example, to measure radial/ulnar deviation.

Sponge spacers 35 are placed under the meter or elastic belts to raise or lower the meter for a level reading (in conjunction with the preferred bubble level) while allowing the part being tested to remain in its neutral or rest position.

In FIG. 6 the cervical chin/1st support plate headband 70 is illustrated. Headband 70 fits over the patient's head for cervical monitoring by way of a hook and loop strip 72 that connects to the hook and loop strip 13 on the bottom of first support plate 10 (FIG. 5). If the fit is loose on the patient, two hook and loop strips 71 at each end of the headband 70 may be connected with the elastic cervical chin strap 60 (FIG. 4) by way its own hook and loop strips 62. This will insure a snug fit on any patient. Headband 70 is also useful on large extremities such as the thigh.

The following statements and reference to illustrations are in regard to the conception and design of the measuring device sometimes referred to herein as a transometer and its ability to precisely measure the transverse ROM of the cervical, thoracic, lumbar, and extremity areas of the human body.

A compass mechanism 20 contains a needle with magnetic north attraction mounted inside a liquid filled vial upon a pivot pin that is placed in the center of a circular 360 degree circumference. This needle remains stationary when the meter is properly rotated.

A rotatable calibrated ring 21 is attached to the outer rim of the vial and is marked, starting with "0" and progresses to "180", moving in either a right or a left direction. The increments from 0 to 180 are in degree units.

This compass mechanism 20 is affixed to a support plate 10 sometimes referred to herein as a 1st support plate and alternatively as a horizontal support surface. A bubble level 30 is affixed as well to the top surface of plate 10. At the rear of the plate 10 there are two 90 degree bends that form a second lower level or lip 11 to used as an attachment site for a 2nd support plate such as extremity plate 42 via its upper level or lip 40 sliding between the bottom surface of the upper level 10 and the top surface of lower level or lip 11 of transometer 5.

The front edge of lip 11 has bevel 12 for easy insertion of lip 40 into slot 14. A hook and loop material strip 13 is attached to the bottom surface of support plate 10 at mid-length (FIG. 5). This is the connection site of the cervical headband 70 via strip 72.

With the 1st and 2nd support plates and cervical headband, the ability to measure cervical, thoracic, lumbar and extremity regions transverse ROM is now possible.

The proper operation and assembly of the transometer aspect of the invention will be appreciated from the following text.

When measuring the thoracic and lumbar areas, two meters are preferably used. Thorax plate 42 is attached to one or both transometers and stabilizer bar 50 is attached to the back of one of the thorax plates via strips 51 and 43. Preferably when testing the thoracic region, the upper meter 80 is hand held by the examiner. The other meter may be attached to a belt 60 that passes around the chest of the patient. Optionally both meters may be hand held, especially during a passive ROM test. As in any reading of any segment, the level should have a centered bubble to insure free needle movement for precision in readings.

Figure 8A:
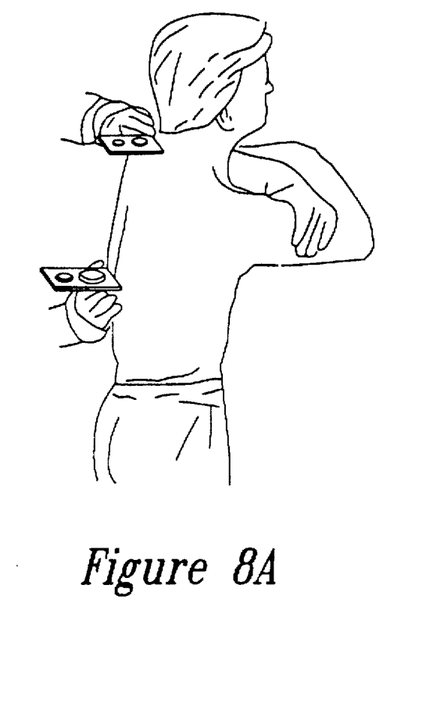
FIGS. 8A and 8B illustrate positioning of an embodiment of the invention on a patient during zeroing (A) and during left lateral torso rotation (B).
Figure 8B:
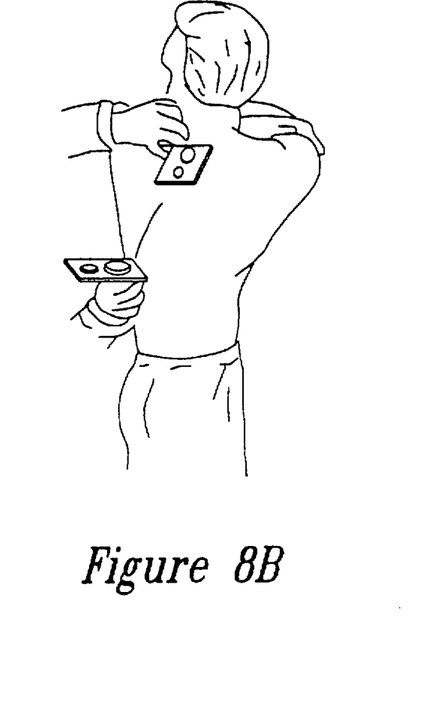

The patient may be standing or sitting (see for instance FIG. 8). Place the transometer 5 with the stabilization bar 50 to the highest area to be measured (ie thoracics at T-1, lumbars at L-1, or for whole thoraco-lumbar area at T-1). The second transometer 5' is to be set at the lowest point to measured (ie thoracics at T-12, lumbars over the sacrum, or for the whole thoraco-lumbar area, over the sacrum).

When placing the meters be sure the bubble in the levels 30 are as close to centered as possible (inside the ring marked on the vial). With the patient in their normal resting position, set the rotating dial of both meters to "0" degrees. This is the patient's "anatomical zero".

Figure 9A:
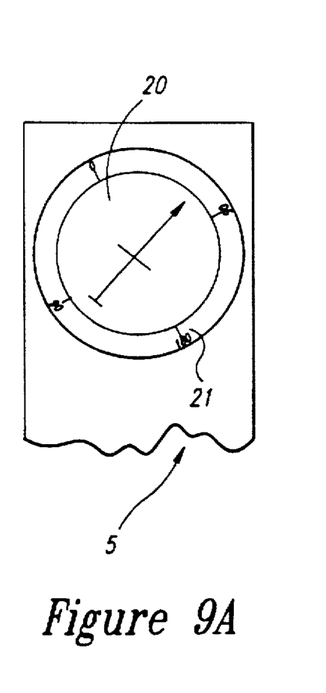
FIGS. 9A through 9C schematically illustrate needle positioning of the transometer on the patient shown in FIG. 8.
Figure 9B:
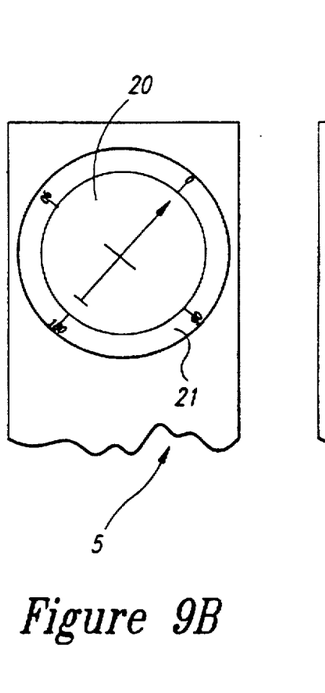
Figure 9C:
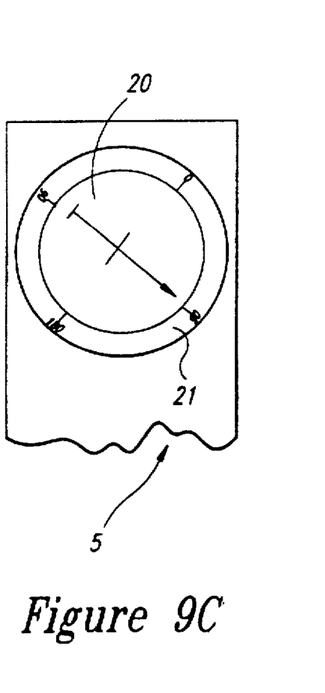

In FIG. 9A (corresponding to patient position in FIG. 8A), transometer 5 is placed for reading, and needle simply points "north". In 9B the slip ring is rotated so north point of needle now points at "0" and the meter is now "zeroed". In 9C (corresponding to patient position in FIG. 8B), meter has rotated with patient, and needle now points on ring to a value corresponding to ROM for that segment or region.

By monitoring the meters with the patient's transverse rotation to the right and then to the left, the examiner can obtain the ROM for each direction by subtracting the bottom reading, that represents the compensation the body has made during the movement, from the top meter's reading that represents the total degrees the body has moved in that particular direction. This simple subtraction gives the examiner the specific number of degrees for that direction's movement.

The patient is rotated in the other direction and process is repeated. There is no need to readjust or "zero" the meters more than once for a complete test for the selected region. This decreases time needed for testing and by the fact that the same anatomical zero is exactly the same for both directions, patient and meter placement errors are removed by setting up once for two directions. One time "zeroing" is followed for all tests whether one meter is use as in cervical testing or two meters are used as in the thoracics and lumbars.

Figure 7A:
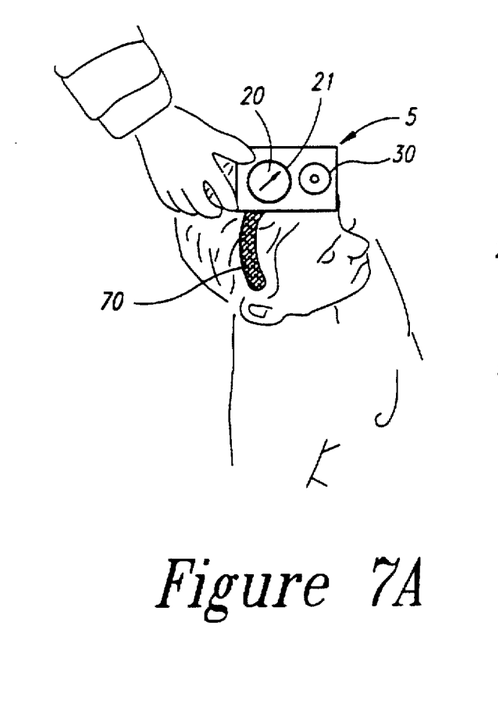
FIGS. 7A and 7B illustrate positioning of an embodiment of the transometer aspect of the invention on a patient during zeroing (A) and during right lateral cervical rotation (B).
Figure 7B:
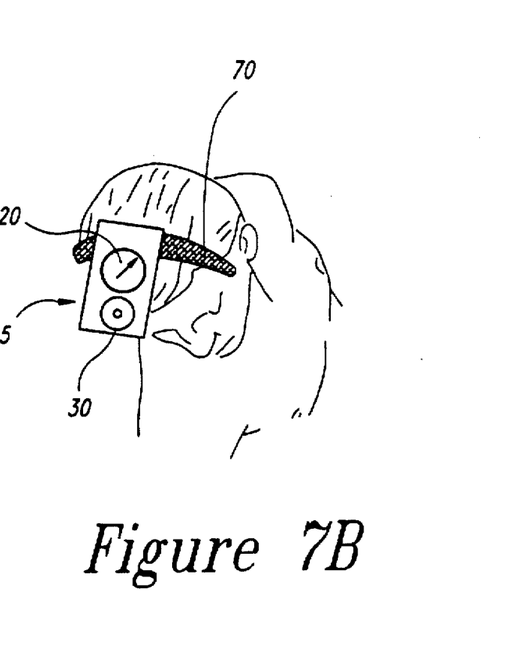

The cervical region is tested in one simple operation (see for example FIG. 7). Connect one transometer 5 to the headband 70 via strip 13 to strip 72. Place the headband on the patient's head with the meter at midline and the patient seated. Have the patient look straight ahead in a "normal" position and then "zero" the needle with ring 21. While stabilizing the patient's shoulders from moving, have them turn right, take your reading, turn left, and take your reading. No meter adjustment need be done and anatomical is once again the same for both readings.

If the headband seems loose, as say on a child, the elastic strap 60 may be attached with the hook and loop connections 62 on the strap connected to the hook and loop strips 71 of headband 70 to assure a snug fit.

When measuring the transverse ROM on the upper and lower extremities, the patient will be standing most of the time. This means that the extremity plate 42 will need to be used along with transometer 5 a good deal of the time. The transverse ROM for extremities can be done with the use of a single meter, an extremity plate, and extremity belt. Attaching the extremity belt 60 to the distal portion of a limb to be tested would be identical to that of a wrist band for a watch. After placing the belt at the location to be measured, the extremity plate 42 with its connected transometer 5 is attached via the attachment sites 41 and 61.

Elastic band 60 is connected to the plate 42 via the hook and loop strips on both components 61 and 41, and then secured around the extremity being tested with the hook and loop strips 62 on the ends of the band connected to each other for a snug yet secure fit.

The same preparation of the patient in normal position and zeroing the meter before testing applies. Whether extremity plate 42 is used, strap 60 only, or just the meter handheld by the doctor, is the option of the doctor. It is anticipated that some patients will need special attention in this regard.

A listing of representative tests for extremities in which the invention can be beneficially used follows:

Cervicals—right and left rotation (seated or standing); flexion and extension (patient lying on side); lateral bending (patient lying supine or prone).

Thoracics—right and left rotation (meters at T-1 and T-12).

Lumbars—right and left rotation (meters at L-1 and L-5).

(Note that with the cervicals, thoracics and lumbars, the use of two meters can also indicate the transverse rotation between a small number of vertebra (as few as two but usually three) in these regions.)

Extremities—(Upper Arm)—Shoulder cuff rotation (abducted 90 degrees, standing, internal and external); humeral pronation and supination (standing); upper extremity abduction and adduction (supine); (Forearm) —pronation and supination (standing); internal and external rotation (flexed and standing); flexion and extension (supine and externally rotated); (Hand)— ulnar deviation (forearm flexed); radial deviation (forearm flexed); (Thigh)—supination and pronation (standing); internal and external rotation (flexed and standing); abduction and adduction (supine); flexion and extension (patient on side); (Lower Leg)— supination and pronation (standing); internal and external rotation (supine, thigh flexed and lower leg flexed); internal and external rotation (standing and lower leg flexed); (Foot)—internal and external rotation (standing) (note that this is mainly for the metering of the supination and pronation of the lower leg).

As the need occurs the apparati and method of the invention can be applied in other possible measurement applications to gauge rotational, flexional, extension movement or the like in transverse or vertical planes. Special care should be taken to stabilize the patient in areas not being tested so the initial readings are as accurate as possible.

Figure 10:
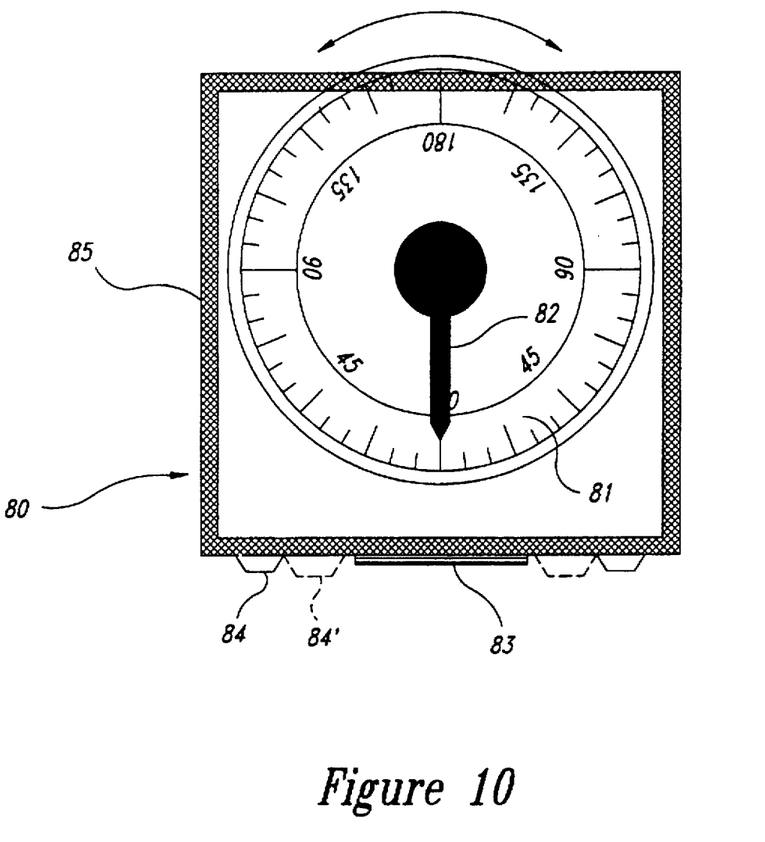
FIG. 10 is a schematic front partial cut away elevation of an embodiment of the inclinometer aspect of the invention.

In FIG. 10 partial cut away schematic of a preferred inclinometer 80 is shown. Free hanging pendulum 82 in case 85 tends, in well known fashion, through the medium of gravity, to always point down, or to the center of the earth. On the bottom of case 85 there is a hook and loop attachment site 83 for connection with other components of the invention such as headband 70, stabilizer bar 50, vertical mode plate 42, and the like. Also on the bottom are feet 84. A zeroing slip ring dial is marked in degree increments as shown for measuring degrees of inclination from the perpendicular (that is to say, "perpendicular" to the normal "surface" or horizon of the earth).

To avoid the possibility of hangup in pivot pins, pivot arms and dip circles of some known devices, a simple, non self centering design of inclinometer is preferred. The preferred meter (either transometer or inclinometer) uses rubber or acrylic feet 84 to "absorb the arc" of the spine or other body part (ie cranium)—actually forming a tangent line approximation to the arc by defining two points with the rubber feet. Preferred embodiments of the inclinometer will have adjustable feet, preferably adjustable by sliding, in ways that will be appreciated by those skilled in the art, from for instance a position shown in the figure at number 84 to a position shown at 84'.

Figure 11A:
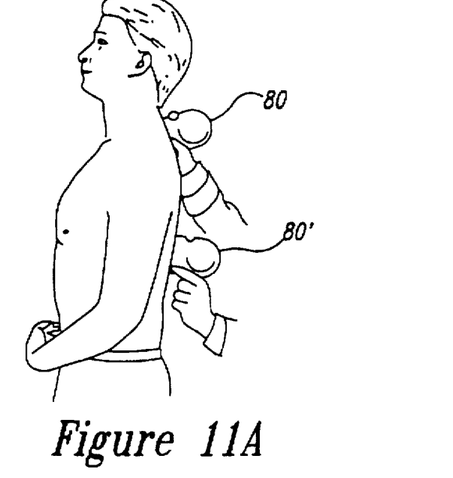
FIGS. 11 through 16 illustrate positioning of an embodiment of the invention on a patient during zeroing and ROM measurement for: standing thoracic flexion (11); seated thoracic flexion (12); supine leg raise (13); cervical flexion and extension (14); cervical left and right lateral flexion (15); and lumbar flexion and extension (16).
Figure 11B:
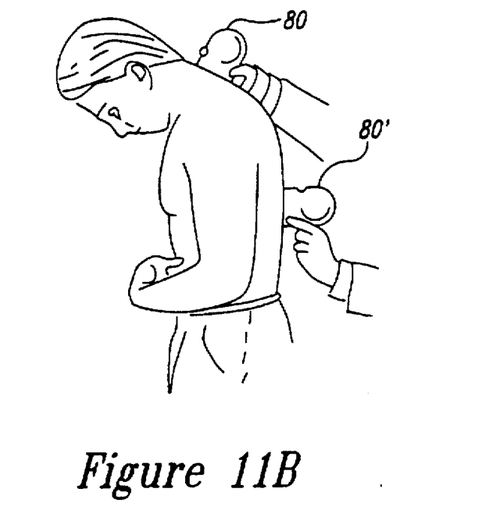

FIGS. 11 through 16 illustrate inclinometer measurements in accordance with the invention to eliminate from measurement the normal patient body compensation movement in the various measurement modalities, as illustrated. FIG. 11 shows inclinometer 80 and below it second inclinometer 80' in measuring standing thoracic flexion. In A, the patient is "normal" and both meters are zeroed. After moving the patient to the position shown in B, both meters will usually show a non zero reading as the lower torso flexes in "compensation" to the movement of the upper torso. The non zero reading from inclinometer 80' is therefore subtracted from the reading of inclinometer 80 to arrive at a "compensation-less" ROM reading for the thoracic ROM for the patient on that day, which is the degree of actual movement of the area being tested.

Figure 12A:
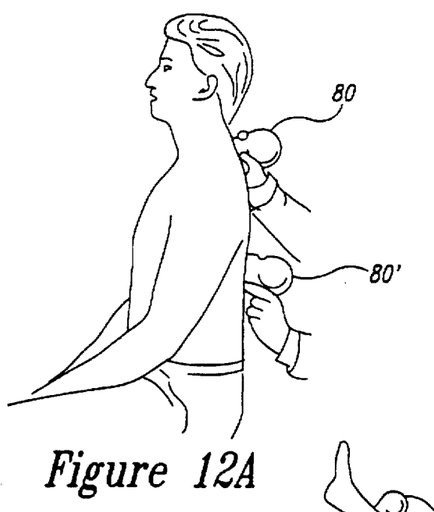
Figure 12B:
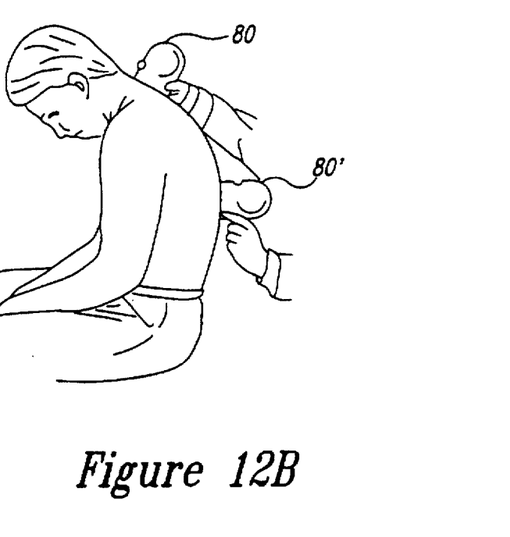
Figure 13:
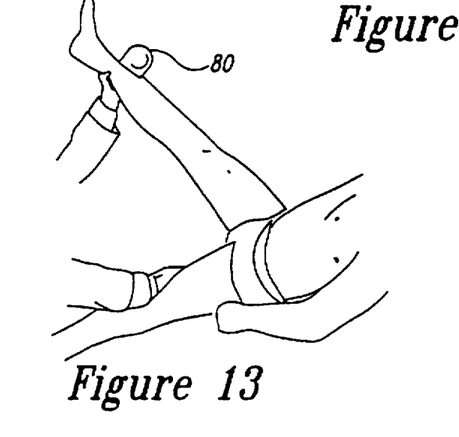
Figure 14A:
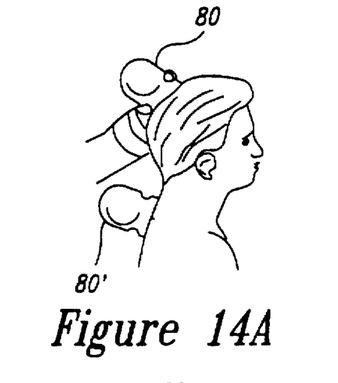
Figure 14B:
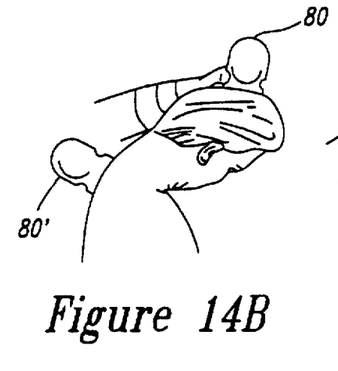
Figure 14C:
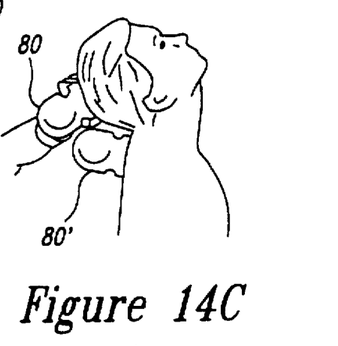
Figure 15A:
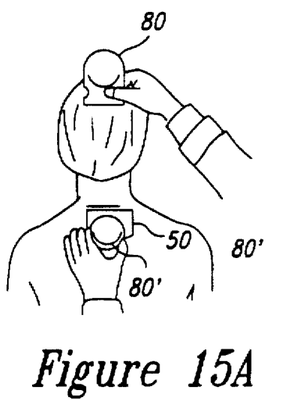
Figures 15B, 15C:
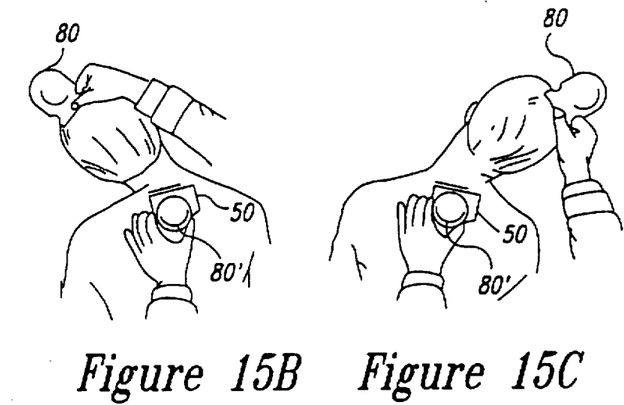
Figure 16A:
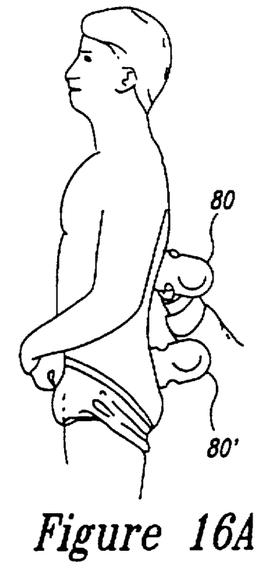
Figure 16B:
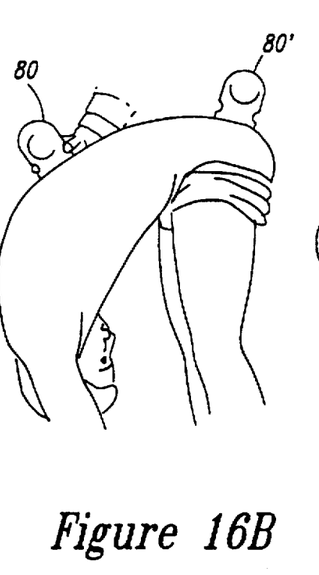
Figure 16C:
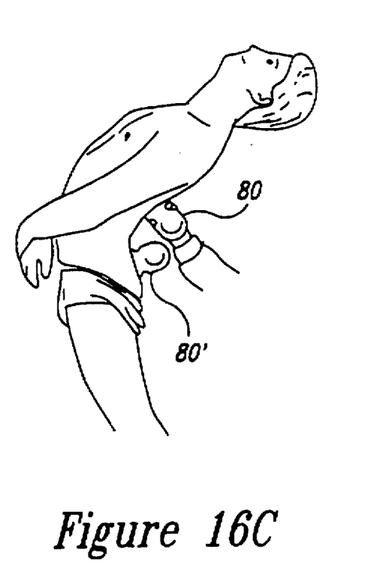

In like manner, FIG. 12 shows seated thoracic flexion, and FIGS. 14 and 16 show zero or "normal" position (A), flexion (B) and extension (C) for cervical and lumbar ROM measurement respectively. FIG. 15 shows zero (A), left cervical lateral flexion (B), and right cervical lateral flexion (C). FIG. 12 shows a typical single meter application to measure supine leg extension (with examiner stabilization in lieu of using a zeroing meter).

Figure 17:
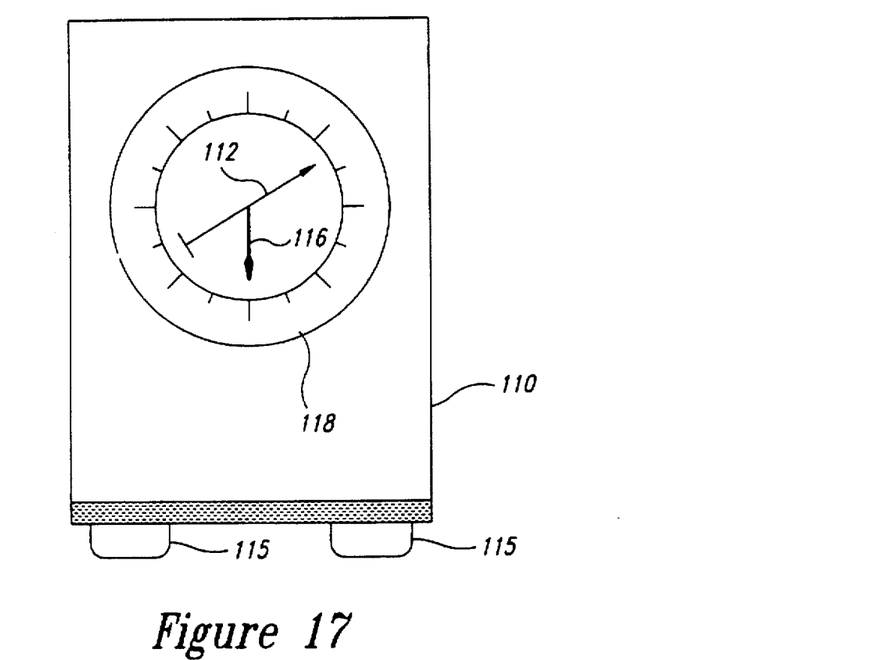
FIG. 17 is a side elevation of an alternate embodiment of the invention.
Figure 18:
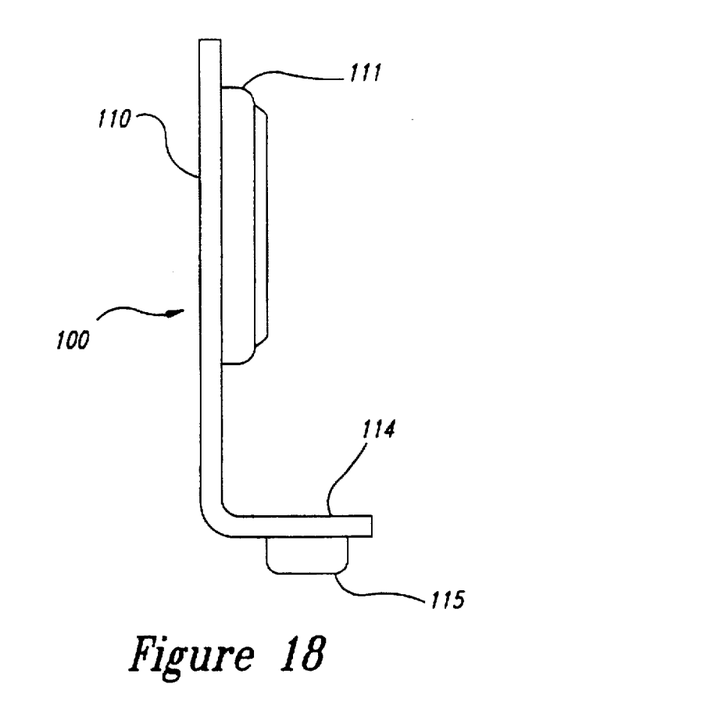
FIG. 18 is a front elevation of an alternate embodiment of the invention.

FIGS. 17 and 18 schematically illustrate an "pocket" embodiment of an aspect of the invention combining in a single structure a magnetic north seeking means, a pendulum type inclinometer, and a right angled plate with feet, thus combining in one structure several components of the invention. Pocket ROM device 100 has a support plate 110 integral at a right angle to which is a foot plate 114 having a pair of feet 115. Inside housing 111 are pivotally disposed a magnetic needle 112 and a pendulum needle 116. On the outside of the housing is a conventional slip ring calibrated dial 118.

In preferred embodiments of the transometer and inclinometer aspects of the invention and all of the above components, preferred dimensions are as follows (with preferred materials noted parenthetically if not generally or commonly known or otherwise made known from the disclosure above):

transometer support plate 10: 3" to 5" long, 2" to 3" wide (clear acrylic, approximately 1/8" thick);

compasses (incl. combined magnetic needle and gravity pendulum model: apx 2.5" dial diameters (available from Brunton in Wyoming);

thorax plate (back/breast plate):generally about 5" long, 2.5" wide (same as transometer);

extremity plate: 2" to 3" long, 2.5" wide (same as transometer);

headband: use commonly available plastic hair headband;

elastic bands: many useful lengths, such as 9"×3/4" or ×1", 52"×1", 13"×1", 16–18"×1 " (generally nylon elastic with hook and loop attachment sites as disclosed herein; however some special purpose bands are special elastic hook and loop material from Toleedo Fasteners in the Los Angeles area and have all of one side in "pile" and substantial stretches of the end zones on the other side in "hooks"; another useful band is a commonly available D-ring ended nylon webbing belt that is mostly pile, including at the D-ring end, and hooks on one side at the other end, much like a thin blood pressure cuff). In one aspect of the invention, a headband 70 is combined with two of the specialty belts disclosed just above to make an elastic head strap cap for mounting multiple transometers and/or inclinometers. The special elastic hook and loop band is connected to strips 71 on headband and stretched around circumference of head with headband 70 preferably at the rear. The pressure cuff like band having been first threaded over the headband through a loop in the band just behind the D-ring, the rest of the strap is brought over the top of the head, under the elastic band at the front of the head and then back on itself to attach, thus providing a plurality of continuous attachment site locations on the head for multiple instrument placement.

In compliance with the statute, the invention has been described in language more or less specific as to structural features. It is to be understood, however, that the invention is not limited to the specific features shown, since the means and construction shown comprise preferred forms of putting the invention into effect. The invention is, therefore, claimed in any of its forms or modifications with the legitimate and valid scope of the appended claims, appropriately interpreted in accordance with the doctrine of equivalents.

I claim:

1. A dual function meter for use in ROM measurement systems, the meter comprising:

a magnetic needle and a pendulum needle, both needles pivotally disposed for pivotal movement about the same axis inside a housing;

the housing mounted upon a support plate, the support plate having connected thereto a foot plate having a pair of feet;

whereby the magnetic needle and the pendulum needle are independently usable to produce ROM measurements.

2. The apparatus of claim 1 wherein the foot plate is connected to the support plate at a right angle.

3. The apparatus of claim 2 wherein the foot plate is connected to the support plate by means of a forming the foot plate from a right angle bend in the support plate.

4. The apparatus of claim 1 further comprising an adjustable slip ring calibrated dial on the housing.

* * * * *